United States Patent
Kramer-Brown et al.

(10) Patent No.: US 8,252,361 B2
(45) Date of Patent: Aug. 28, 2012

(54) IMPLANTABLE MEDICAL DEVICES FOR LOCAL AND REGIONAL TREATMENT

(75) Inventors: Pamela A. Kramer-Brown, San Jose, CA (US); Florian Ludwig, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1188 days.

(21) Appl. No.: 11/946,768

(22) Filed: Nov. 28, 2007

(65) Prior Publication Data

US 2009/0053392 A1 Feb. 26, 2009

Related U.S. Application Data

(63) Continuation-in-part of application No. 11/810,518, filed on Jun. 5, 2007, now abandoned.

(51) Int. Cl.
*A61L 33/00* (2006.01)

(52) U.S. Cl. ........ 427/2.1; 623/1.38; 623/1.15; 424/423; 525/413; 427/2.24; 427/2.25; 427/421.1; 427/424; 427/425; 427/427.3; 427/427.4; 427/427.5

(58) Field of Classification Search .................. 424/423; 525/413; 623/1.15, 1.38
See application file for complete search history.

(56) References Cited

U.S. PATENT DOCUMENTS

| | | | |
|---|---|---|---|
| 4,304,767 A | 12/1981 | Heller et al. | |
| 4,733,665 A | 3/1988 | Palmaz | |
| 4,800,882 A | 1/1989 | Gianturco | |
| 4,886,062 A | 12/1989 | Wiktor | |
| 4,916,193 A * | 4/1990 | Tang et al. | 525/413 |
| 5,124,219 A | 6/1992 | Shintani et al. | |
| 5,581,387 A | 12/1996 | Cahill | |
| 5,858,556 A | 1/1999 | Eckert et al. | |
| 5,861,387 A | 1/1999 | Labrie et al. | |
| 5,977,163 A | 11/1999 | Li et al. | |
| 6,413,272 B1 * | 7/2002 | Igaki | 623/1.15 |
| 6,503,538 B1 | 1/2003 | Chu et al. | |
| 6,703,040 B2 | 3/2004 | Katsarava et al. | |
| 6,780,424 B2 | 8/2004 | Claude | |
| 7,056,591 B1 | 6/2006 | Pacetti et al. | |
| 7,166,680 B2 | 1/2007 | DesNoyer et al. | |
| 7,202,325 B2 | 4/2007 | Hossainy et al. | |
| 7,220,816 B2 | 5/2007 | Pacetti et al. | |
| 7,396,538 B2 | 7/2008 | Granada et al. | |
| 7,910,152 B2 | 3/2011 | Kleiner et al. | |
| 8,048,442 B1 | 11/2011 | Hossainy et al. | |
| 2002/0082679 A1 | 6/2002 | Sirhan et al. | |
| 2002/0156150 A1 | 10/2002 | Williams et al. | |

(Continued)

FOREIGN PATENT DOCUMENTS

EP 1 607 109 12/2005

(Continued)

OTHER PUBLICATIONS

International Search Report for PCT/US2008/082620, mailed Feb. 8, 2010, 13 pgs.

(Continued)

*Primary Examiner* — David Turocy
*Assistant Examiner* — Andrew Bowman
(74) *Attorney, Agent, or Firm* — Squire Sanders (US) LLP

(57) ABSTRACT

Implantable medical devices adapted to erodibly release delivery media for local and regional treatment are disclosed.

12 Claims, 6 Drawing Sheets

U.S. PATENT DOCUMENTS

| | | | |
|---|---|---|---|
| 2002/0197178 A1 | 12/2002 | Yan | |
| 2004/0024450 A1 | 2/2004 | Shulze et al. | |
| 2004/0185081 A1* | 9/2004 | Verlee et al. | 424/423 |
| 2005/0055075 A1 | 3/2005 | Pinchuk et al. | |
| 2005/0106204 A1 | 5/2005 | Hossainy et al. | |
| 2005/0112171 A1 | 5/2005 | Tang et al. | |
| 2005/0137381 A1 | 6/2005 | Pacetti et al. | |
| 2005/0208091 A1 | 9/2005 | Pacetti | |
| 2005/0245637 A1 | 11/2005 | Tang et al. | |
| 2005/0265960 A1 | 12/2005 | Pacetti et al. | |
| 2005/0271700 A1 | 12/2005 | DesNoyer et al. | |
| 2005/0283229 A1* | 12/2005 | Dugan et al. | 623/1.38 |
| 2006/0089485 A1 | 4/2006 | DesNoyer et al. | |
| 2006/0093842 A1 | 5/2006 | DesNoyer et al. | |
| 2006/0115513 A1 | 6/2006 | Hossainy | |
| 2006/0142541 A1 | 6/2006 | Hossainy | |
| 2006/0147412 A1 | 7/2006 | Hossainy et al. | |
| 2006/0246109 A1 | 11/2006 | Hossainy et al. | |
| 2006/0271168 A1 | 11/2006 | Kleine et al. | |
| 2007/0055364 A1 | 3/2007 | Hossainy et al. | |
| 2007/0134288 A1 | 6/2007 | Parsonage et al. | |
| 2007/0198081 A1 | 8/2007 | Catro et al. | |
| 2007/0254012 A1 | 11/2007 | Ludwig et al. | |
| 2007/0280988 A1* | 12/2007 | Ludwig et al. | 424/423 |
| 2007/0286882 A1 | 12/2007 | Tang | |
| 2008/0124372 A1 | 5/2008 | Hossainy et al. | |
| 2008/0161906 A1 | 7/2008 | Atanasoska et al. | |
| 2008/0305141 A1 | 12/2008 | Hossainy et al. | |
| 2009/0326645 A1 | 12/2009 | Pacetti et al. | |
| 2010/0145436 A1 | 6/2010 | Weber et al. | |
| 2011/0086162 A1 | 4/2011 | Hossainy et al. | |
| 2011/0151104 A1 | 6/2011 | Kleiner et al. | |
| 2011/0153004 A1 | 6/2011 | Kleiner et al. | |
| 2011/0200660 A1 | 8/2011 | Kleiner et al. | |

FOREIGN PATENT DOCUMENTS

| | | |
|---|---|---|
| WO | WO 00/74744 | 12/2000 |
| WO | WO 2004/060428 | 7/2004 |
| WO | WO 2005/102222 | 11/2005 |
| WO | WO 2006/074391 | 7/2006 |
| WO | WO 2007/106247 | 9/2007 |
| WO | WO 2007/123872 | 11/2007 |
| WO | WO 2007/126598 | 11/2007 |
| WO | WO 2008/151299 | 12/2008 |

OTHER PUBLICATIONS

U.S. Appl. No. 10/816,072, filed Mar. 31, 2004, Dugan et al.
U.S. Appl. No. 10/931,853, filed Aug. 31, 2004, Hossainy et al.
U.S. Appl. No. 11/007,944, filed Dec. 8, 2004, Gale et al.
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
De Lezo et al., *Intracoronary Ultrasound Assessment of Directional Coronary Atherectomy: Immediate and Follow-Up Findings*, JACC vol. 21, No. 2, (1993) pp. 298-307.
Moreno et al., *Macrophage Infiltration Predicts Restenosis After Coronary Intervention in Patients with Unstable Angina*, Circulation, vol. 94, No. 12, (1996) pp. 3098-3102.
Oikawa et al., *Mechanisms of Acute Gain and Late Lumen Loss After Atherectomy in Different Preintervention Arterial Remodeling Patterns*, The Am. J. of Cardiology, vol. 89, (2002) pp. 505-510.
Scully et al., *Effect of a heparan sulphate with high affinity for antithrombin III upon inactivation of thrombin and coagulaton Factor Xa*, Biochem J. 262, (1989) pp. 651-658.
Virmani et al., *Lessons From Sudden Coronary Death a Comprehensive Morphological Classification Scheme for Atherosclerotic Lesions*, Arterioscler Thromb Vasc Biol. (2000) pp. 1262-1275.
U.S. Appl. No. 11/187,467, filed Jul. 22, 2005, Desnoyer et al.
U.S. Appl. No. 11/847,222, filed Aug. 29, 2007, Hsu et al.
International Search Report for PCT/US2007/002398, mailed Apr. 22, 2008, 6 pgs.
International Search Report for PCT/US2008/065981, mailed Jan. 20, 2010, 22 pgs.
EP Examination report for 08770236.1, mailed Mar. 23, 2011, 5 pgs.
Park et al. "Membrane formation by water vapor induced phase inversion", J. of Membrane Science, vol. 156, pp. 169-178 (1999).

* cited by examiner

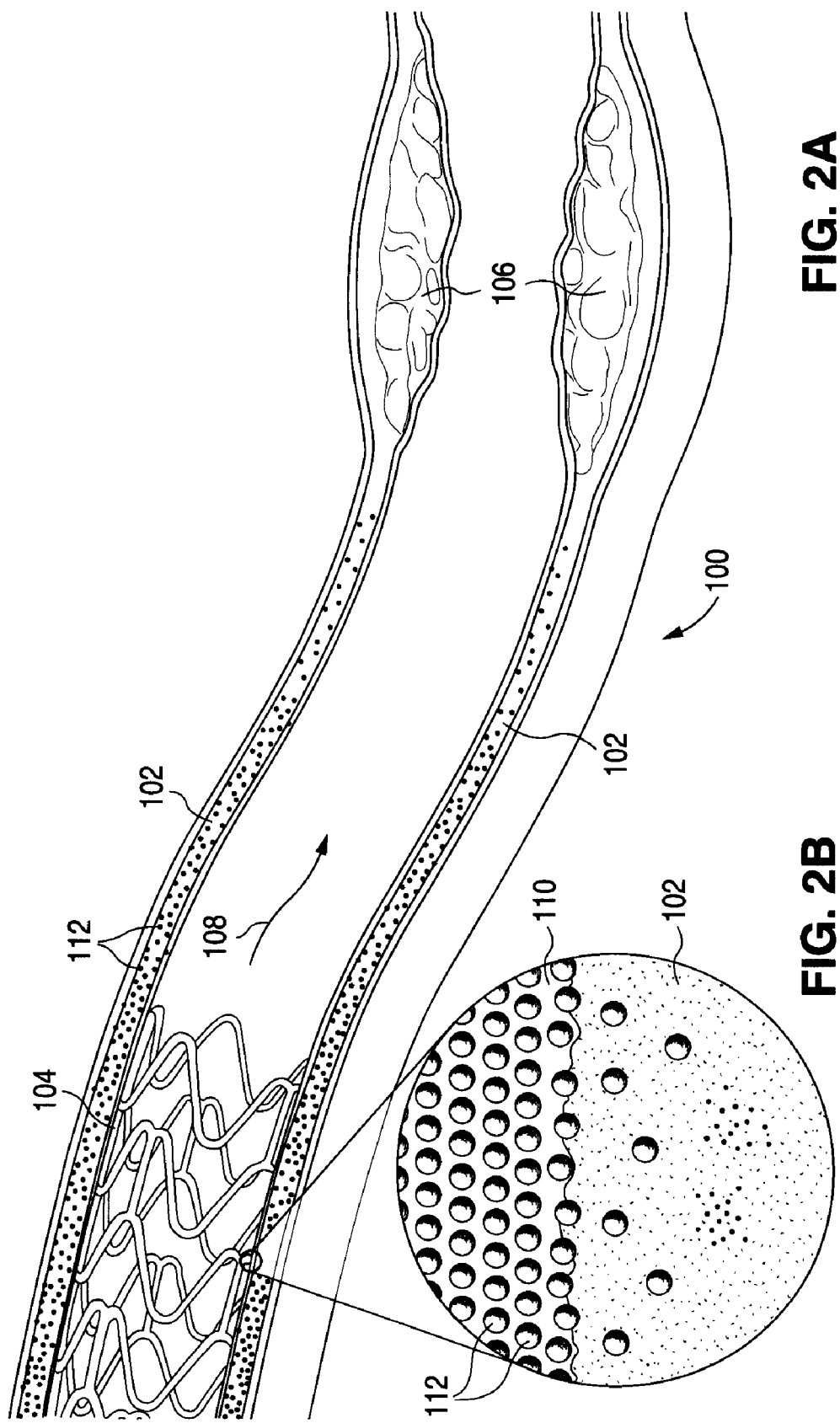

FIG. 6A
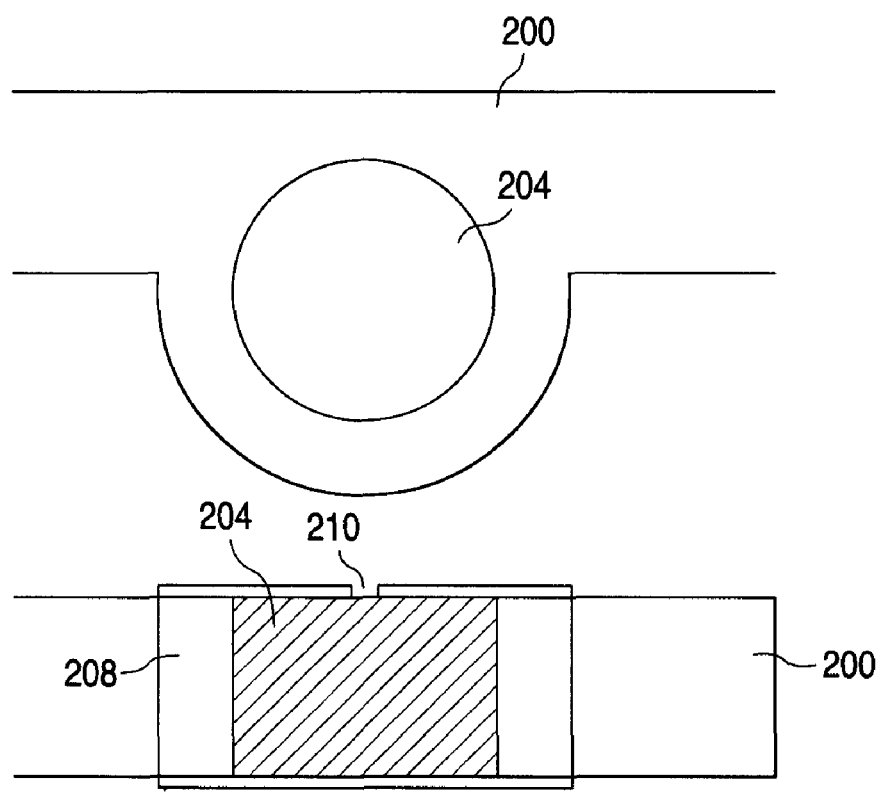
FIG. 6B
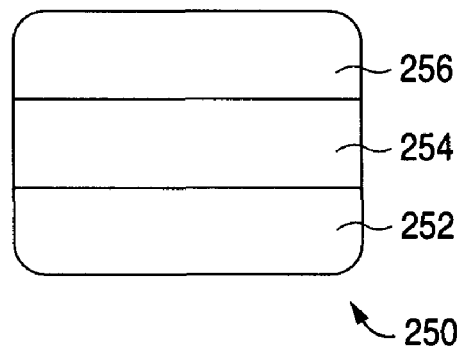
FIG. 8

FIG. 7A
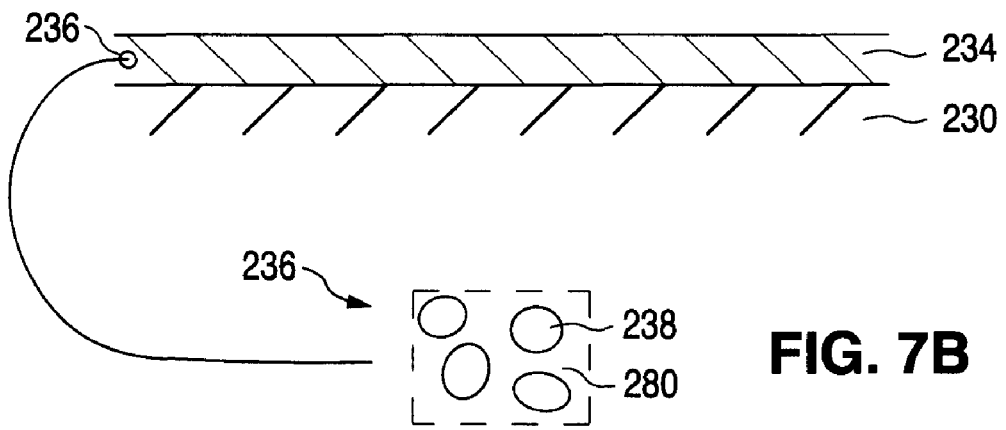
FIG. 7B
FIG. 7C
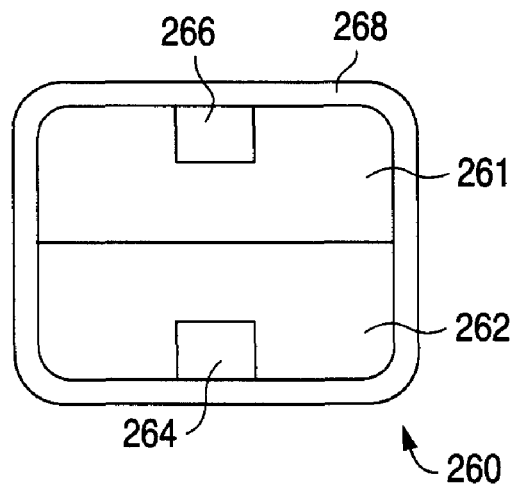
FIG. 9

IMPLANTABLE MEDICAL DEVICES FOR LOCAL AND REGIONAL TREATMENT

RELATED APPLICATIONS

This application is a Continuation-In-Part of U.S. patent application Ser. No. 11/810,518 filed Jun. 5, 2007, entitled "Implantable Medical Devices for Local and Regional Treatment".

BACKGROUND OF THE INVENTION

1. Field of the Invention

This invention relates to implantable medical devices adapted to deliver media for local and regional treatment.

2. Description of the State of the Art

This invention relates generally to implantable medical devices for treating bodily disorders. A typical treatment regimen with an implantable medical device involves implantation of a device at a selected treatment location. During treatment it may be necessary for the device to support body tissue. Therefore, the structure of a device may include load bearing structural elements or substrate to hold the device in place and to resist forces imposed by surrounding tissue.

The treatment of a bodily disorder may also involve local delivery of a bioactive agent or drug to treat a bodily disorder. The agent may be incorporated into the device in a variety of ways and delivered directly to an afflicted region at or adjacent to a region of implantation.

Additionally, in many treatment situations, the presence of the device is required only for a limited period of time. Therefore, a device may be composed in whole or in part of materials that degrade, erode, or disintegrate through exposure to conditions within the body until the treatment regimen is completed.

An example of such devices includes radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be capable of withstanding the structural loads, namely radial compressive forces, imposed on the stent as it supports the walls of a vessel. Therefore, a stent must possess adequate radial strength, which is the ability of a stent to resist radial compressive forces. Once expanded, the stent must adequately maintain its size and shape throughout its service life despite the various forces that may come to bear on it, including the cyclic loading induced by the beating heart. In addition, the stent must possess sufficient flexibility to allow for crimping, expansion, and cyclic loading.

The structure of a stent is typically composed of scaffolding or substrate that includes a pattern or network of interconnecting structural elements often referred to in the art as struts or bar arms. The scaffolding can be formed from wires, tubes, or sheets of material rolled into a cylindrical shape. The scaffolding is designed so that the stent can be radial'y compressed (to allow crimping) and radially expanded (to allow deployment).

Additionally, a drug-eluting stent may be fabricated by coating the surface of either a metallic or polymeric scaffolding with a polymeric carrier that includes an active or bioactive agent or drug. Polymeric scaffolding may also serve as a carrier of an active agent or drug. Currently drugs or drug mixtures are typically released from coatings through diffusion or elution through coating. In addition, for pure drugs dispersed in coatings, the time frame of the therapeutic effect of the drug is relatively short. As a result, the treatment is limited to a region local to the region of implantation of the stent.

In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers can be configured to completely erode after the clinical need for them has ended.

In some treatment situations, local treatment of bodily tissue disorders with an implantable medical device may be difficult or insufficient. This insufficiency may be from the fact that tissue disorders may be diffuse and in multiple locations. Local treatment in such situations may require a multiplicity of devices. For example, vascular disorders can include lesions in multiple locations, such as diffuse lesions along vessels, multi-vessel lesions, and bifurcated vessel lesions. In addition, local treatment may be impossible because an afflicted region of tissue may be inaccessible to implantation of a device. For example, a diseased vessel may be too small for implantation of a stent. Thus, it would be desirable to have an implantable medical device that can be used to treat tissue disorders both local and regional to the location of implantation.

SUMMARY OF THE INVENTION

Certain embodiments of the present invention include a stent comprising a scaffolding formed from a corrodible metal having one or more recesses in a surface of the scaffolding, the recesses being at least partially filled with a plurality of releasable delivery media comprising an active agent, wherein the active agent is adapted to be released from the delivery media upon release of the delivery media from an implanted stent.

Certain embodiments of the present invention include a stent partially or wholly formed from a mixture that includes multiple polymers dissolved in multiple immiscible solvents. Particles of one polymer disperse within a matrix of another polymer and release from the matrix upon stent implantation. The invention may also include active agents incorporated within the mixture for delivery from an implanted stent.

BRIEF DESCRIPTION OF THE DRAWINGS

FIG. 2A depicts a section of a blood vessel with an implanted stent.

FIG. 2B depicts an expanded portion of an interface between an erodible matrix of a stent having embedded delivery particles.

FIG. 6A depicts an overhead view of a stent strut with a well containing active agent or delivery media.

FIG. 6B depicts a side view of the strut of FIG. 6A showing a coating layer disposed above the well.

FIG. 7A depicts a delivery media layer over a corrodible metallic substrate.

FIG. 7B depicts an expanded portion of the layer in FIG. 7A.

FIG. 7C a topcoat layer over a delivery media layer over a corrodible metallic substrate.

FIG. 8 depicts a cross-section of a strut of a stent with three polymer layers.

FIG. 9 depicts a cross-section of a layered strut.

DETAILED DESCRIPTION OF THE INVENTION

Embodiments of the present invention can generally be applied to implantable medical devices including, but not limited to, self-expandable stents, balloon-expandable stents, stent-grafts, vascular grafts other expandable tubular devices for various bodily lumen or orifices. The embodiments can be used in the local and regional treatment bodily disorders in various bodily lumens, including, but not limited to vulnerable plaque, atherosclerotic progression, and diabetic nephropathy.

Figure 1:
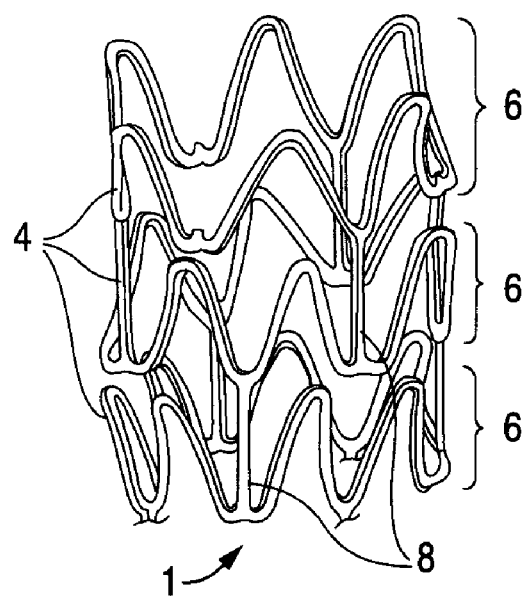
FIG. 1 depicts a view of a stent.

FIG. 1 depicts a view of a stent 1 which is made up of struts 4. Stent 1 has interconnected cylindrical rings 6 connected by linking struts or links 8. The embodiments disclosed herein are not limited to stents or to the stent pattern illustrated in FIG. 1. The embodiments are easily applicable to other stent patterns and other devices. The variations in the structure of patterns are virtually unlimited.

A stent such as stent 1 may be fabricated from a tube by forming a pattern with a technique such as laser cutting. Representative examples of lasers that may be used include an excimer, carbon dioxide, and YAG. In other embodiments, chemical etching may be used to form a pattern on the elongated tube.

As discussed above, the current state of the art includes a drug-eluting stent that has a coating on its surface with a polymeric carrier that includes an active or bioactive agent or drug dispersed in pure form throughout the carrier. Upon implantation, the active agent diffuses or elutes through the carrier and is released into a lumen. The therapeutic effect of the eluted agent is limited to the region immediately adjacent to the implanted stent.

Various embodiments of the present invention relate to implantable medical devices, such as a stent, for treating bodily tissue disorders with therapeutic agents both locally and regionally. Regional treatment refers to treatment of regions of bodily tissue that are proximal and/or distal to an implantation site. In some embodiments, the stent can be biodegradable so that it can disintegrate and disappear from the region of implantation once treatment is completed.

In some embodiments, a plurality of releasable delivery media may be incorporated within or on an implantable medical device. The delivery media can be released from the stent upon implantation. In certain embodiments, the delivery media can be transported distal to the implant site. An active agent incorporated in or on the delivery media may released from the delivery media in a sustained manner. As a result, delivery from the delivery media can occur both locally and regionally over an extended time frame.

As discussed in more detail below, a delivery medium can be, for example, a particle with an active agent encapsulated or dispersed within, adsorbed to the surface of or absorbed within the outside surface of the delivery particle. Alternatively, the delivery particle may be formed by a precipitate of a bioactive agent, e.g., by a neat bioactive agent or a salt of the bioactive agent with low solubility. The active agent included can be released from the delivery media into a patient's body after release of the delivery media from the device. The delivery media allows for sustained-release of active agent from the delivery media into the body after release of the delivery media from the stent implant.

As used herein, the term "sustained release" generally refers to a release profile of an agent or drug that can include zero-order release, exponential decay, step-function release or other release profiles that carry over a period of time, for example, ranging from several hours to several years, preferably from several days to several months, most preferably from several days to several weeks. The terms "zero-order release", "exponential decay" and "step-function release" as well as other sustained release profiles are well known in the art (see, for example, Encyclopedia of Controlled Drug Delivery, Edith Mathiowitz, Ed., Culinary and Hospitality Industry Publications Services).

Delivery media may be incorporated into or onto a stent implant in various ways, as described in more detail herein. For example, the media can be disposed within depots or holes at the surface of the substrate, disposed in a coating on the surface of the substrate, or embedded or dispersed in the substrate of the stent implant. In one embodiment, the release of the media may be due in whole or in part to erosion or degradation of coating material, substrate material, or material which binds the delivery media to or within the stent implant. In further embodiments, the released media can be transported away from a region of implantation to a distal and/or proximal region after being released. The active agent can be released from the media during transport resulting in treatment of distal and/or proximal regions with the active agent.

FIGS. 2A and 2B provide a schematic illustration of regional treatment with a stent. FIG. 2A depicts a section of a blood vessel 100 having vascular walls 102. A stent 104 is implanted distal to a non-flow limiting lesion 106. Delivery media, such as particles, can be selectively or directionally disposed on abluminal faces, luminal faces, both abluminal and luminal faces, and sidewalls of a stent. Selectively disposing particles in this manner allows for directional release of the particles and drug release to a targeted region. As depicted in FIG. 2A, the delivery particles 112 are released from stent 104 into the tissue of vascular wall 102. Particles can be selected that can diffuse through the tissue of vascular wall 102 and deliver both locally and to a distal and/or proximal region of vasculature, such as lesion 106.

FIG. 2B depicts an expanded portion of an interface between an erodible matrix 110 of stent 104 having embedded delivery particles. Erodible matrix 110 can be material disposed within a depot in stent 104, a coating over stent 104, or the scaffolding of stent 104.

Delivery particles can also be released into the blood stream for treatment of distal and/or proximal vasculature after implantation. Delivery particles can be released from the stent into the interior of the lumen, for example, from a luminal face of the stent. The released particles can be transported downstream as shown by an arrow 108 of the implanted stent 104 to a proximal or distal regions of vasculature, such as lesion 106. In some embodiments, particles may be designed to have or selected to have an affinity to a portion of a proximal or distal region of the vasculature. Such particles may selectively bind to a portion, e.g., by incorporating a peptide or an antibody fragment with affinity to receptors found on endothelial cells of the microvasculature into the surface of the particles.

In certain embodiments, the scaffolding or substrate of the implantable medical device can be fabricated from a biostable or non-corrodible material. Such a material can be a biostable polymer, non-corrodible metal, or a combination thereof.

As discussed above, an implantable medical device, such as a stent scaffolding or substrate, can be fabricated from a material that erodes or disintegrates upon implantation into the body. The terms degrade, absorb, and erode, as well as degraded, eroded, and absorbed, are used interchangeably and refer to materials that are capable of being completely eroded, or absorbed when exposed to bodily conditions. The term "corrosion" or "corrode" is typically used to refer erosion of a metal. Such materials may be capable of being gradually resorbed, absorbed, and/or eliminated by the body. A device made of such materials may disintegrate and disappear from a region of implantation once a treatment is completed.

The duration of a treatment period depends on the bodily disorder that is being treated. In treatments of coronary heart disease involving use of stents in diseased vessels, the duration can be in a range from about a week to a few years. However, the duration is typically in a range from about six to twelve months.

In certain embodiments, a stent scaffolding or substrate can be formed in whole or in part of a corrodible metal. The metal selected for use in an implantable medical device in accordance with the present invention may include a single element, such as iron, or may include a combination of metals. Generally, the metal(s) must be implantable without causing significant inflammation, neointimal proliferation or thrombotic events and must be corrodible so as to dissolve, dissociate or otherwise break down in the body without significant ill effect.

In one embodiment, the corrodible metal can be a metal that has a propensity for self-dissolution in an in vivo environment. A metal that undergoes self-dissolution in an in vivo environment corrodes when subjected to bodily fluids and breaks down. A self-dissolving metal can be selected that has little or no ill effect to a patient. Representative examples of self-dissolving metals in an in vivo environment include, but are not limited to, Mg, Mn, K, Ca, Na, Zn, Cr, Fe, Cd, Al, Co, Sb, Sn, V, Cu, W, and Mo.

Alternatively, the corrodible metal may include a combination of two or more metals selected to create a galvanic couple such that the material will undergo galvanic dissolution upon contact with bodily fluids. Reliance on galvanic corrosion in order to achieve a desired corrosion rate requires the selection of a metal pair that has a sufficiently high rest potential differential. A rest potential differential results from two metals that, by themselves, each have a particular rest potential when measured versus a reference electrode, for example a Standard Calomel Electrode (SCE) or Natural Hydrogen Electrode (NHE), in the same type of solution, for example saline or equine horse serum. The driving force toward corrosion that results from this differential may be tailored to control the rate of degradation of the joined materials. For example, a driving force of about 500 mV would generally result in a slower dissolution than a driving force of 1 V or more. Appropriate metal pairs can be selected from among the elements Mg, Mn, K, Ca, Na, Zn, Cr, Fe, Cd, Al, Co, Sb, V, Cu, and Mo, and from alloys based on such elements.

The degradation rate may be tailored by selecting a combination of metals that have a driving force of about 500 mV or greater. In one embodiment the driving force would be about 1 V or greater. For example, Ti has a rest potential of 3.5 V vs. SCE in equine serum, and would, when paired with almost any other metal, yield a suitable driving force. Alternatively, the pairings Nb—Cr (1.1 V rest potential differential vs. SCE in equine serum), Pd—W (1.23 V rest potential vs. SCE in equine serum), Cr—W (630 mV rest potential differential vs. SCE in equine serum), and Ir—Zn (830 mV rest potential differential vs. SCE in equine serum) would also yield suitable driving forces.

In some embodiments, the stent can be formed of a porous corrodible metal. The pores increase the surface area of contact of bodily fluids which tends to accelerate the corrosion rate of the metal. By selecting the metal and the degree of porosity, the rates of degradation can be tailored to a range of applications. The porosity has a substantial effect on the rate of corrosion to the extent that the ratio of corrosion rate increase to surface area increase has been found to vary from 0.3 to 1.0 depending on the type of material and the environment to which it is exposed. The morphology of the microcellular porous metal, including the cell size and porosity of the metal, can be controlled so that the cell sizes can be made very uniform, and can be controlled precisely by the manipulation of various parameters during the formation process. The desired porosity is achievable by a variety of techniques including, but not limited to sintering, foaming, extrusion, thixomolding, semi-solid slurry casting and thermal spraying. The stent structure may be formed using any of the well known techniques, including, for example, laser cutting of a tubular form.

In some embodiment, a device, coating, or binder for the delivery media, or more specifically, particles, can be composed of a biodegradable or water soluble polymer. In general, polymers can be biostable, bioabsorbable, biodegradable, or bioerodable. Biostable refers to polymers that are not biodegradable. The terms biodegradable, bioabsorbable, bioerodable, and soluble, as well as degraded, eroded, absorbed, and dissolved are used interchangeably and refer to polymers that are capable of being completely eroded, absorbed, or dissolved after implantation, e.g., when exposed to bodily fluids such as blood and can be gradually resorbed, absorbed, and/or eliminated by the body. The mechanism of absorption or clearance is entirely different for a bioerodible versus a biosoluble polymer.

As discussed above, the delivery media can include particles that include active agent(s). The particles can be nanoparticles or microparticles. A nanoparticle refers to a particle with a characteristic length (e.g., diameter) in the range of about 1 nm to about 1,000 nm. A microparticle refers to a particle with a characteristic length in the range of greater than 1,000 nm and less than about 10 micrometers. Methods for the manufacture of microparticles are well known to those skilled in the art. Microparticles are commercially available from a number of sources (for example: Alkermes Inc. Cambridge Mass.).

Particles may have active agents mixed, dispersed, or dissolved in the particle material. The particle material can be a biostable or biodegradable polymer, metallic, or ceramic. Such particles may also be coated with an active agent. The particles can also encapsulate one or more active agents by having an outer shell of polymer, metal, or ceramic with an inner compartment containing one or more active agents. Alternatively, the particle may be formed from a precipitate of neat drug.

In some embodiments, particles may be designed to use a combination of the above, e.g., a particle may include a polymeric and a drug, or a drug- or agent-impregnated core coated with a bioerodible metal. In addition, particles may include fullerenes coated with a bioactive agent. Particles may also include polymerosomes, micelles, vesicles, liposomes, glass (biodegradable and biostable), and micronized drug.

Representative examples of materials that may be used for particles include, but are not limited to, a biostable polymer; a bioabsorbable polymer; a biosoluble material; a biopolymer; a biostable metal; a bioerodible metal; a block copolymer of a bioabsorbable polymer or a biopolymer; a ceramic material such as a bioabsorbable glass; salts; fullerenes; lipids; carbon nanotubes; or a combination thereof.

A "micelle" refers to an aggregate (or cluster) of surfactant molecules. "Surfactants" refer to chemicals that are amphipathic, which means that they contain both hydrophobic and hydrophilic groups. Micelles tend to form when the concentration of surfactant is greater than a critical micelle concentration. Micelles formed from block copolymers and/or lipids may be loaded with active agent. Micelles can exist in different shapes, including spherical, cylindrical, and discoidal. Micelles may be stabilized by crosslinking of the surfactant molecules that form the micelle.

Additionally, vesicles formed from block copolymers and or lipids can be loaded with bioactive agent. A vesicle is a relatively small and enclosed compartment or shell formed by at least one lipid bilayer. The vesicle may also be stabilized by crosslinking the lipid bilayer shell.

In some embodiments, delivery particles can be incorporated into a device substrate, coating, or depots in a substrate with a binder that holds the particles together within or on the device. In an embodiment, a surfactant may be utilized to enhance integration of the particles into the binder matrix. The binder may be composed in whole or in part of an erodible binder material. The particles may then be released from the device upon erosion of the binder material. Representative examples of materials that may be used for a binder include, but are not limited to, a bioabsorbable polymer; a biostable, but biosoluble polymer; a biosoluble material; a biopolymer; a biostable metal; a bioerodible metal; a block copolymer of a bioabsorbable polymer or a biopolymer; salts; bioerodible glass; or a combination thereof.

Additionally, delivery particles may be surface-modified to allow targeted delivery of biopharmaceuticals to bodily tissue. Such surface modification could be with antibodies or their fragments, small-molecular ligands, or specific receptors.

Various embodiments of the present invention include an implantable medical device, such as a stent implant, having releasable delivery media. Such delivery media provides sustained-release of active agent for treatment both locally and regionally to a site of device implantation.

Certain embodiments of a device can include a substrate or scaffolding of a stent formed from a corrodible metal having one or more recesses in a surface of the substrate. The recesses can be at least partially filled with delivery media that includes active agent(s). The delivery media allows for sustained release of an active agent from the media upon release of the media from the device.

Recesses can include, for example, depots or channels at a surface of a substrate of a device. Numerous embodiments of depots or channels configured to hold delivery media are possible. Depots, for example, may be placed at one or more arbitrary locations on a device. In addition to recesses, hollow struts could be configured to increase delivery media loading. Such hollow struts can be made by methods known by one of ordinary skill in the art.

Figure 3:
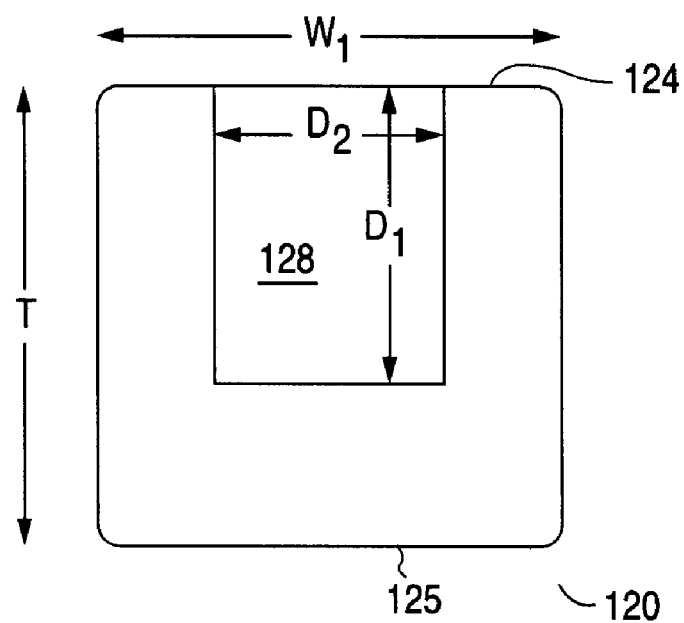
FIG. 3 depicts a cross-section of a strut of a stent illustrating the geometry of an exemplary depot.

FIG. 3 depicts a cross-section of a strut 120 of a stent illustrating the geometry of an exemplary depot 128 disposed at an abluminal face 124 of strut 120. Strut 120 has a width $W_1$. Depot 128 has a generally cylindrical shape with a depth $D_1$ and diameter $D_2$. The appropriate values for $D_1$ and $D_2$ depend on factors such as the effective delivery media, mechanical integrity of the strut, density of depots, and the desired time frame of release of the delivery media. For instance, the greater the effective amount of delivery media, and active agent(s) contained therein, the larger either or both depth $D_1$ and diameter $D_2$ may need to be. A higher density of depots disposed on a strut may decrease a required amount of delivery media in an individual strut, and thus a necessary size of a depot. Furthermore, as the size and density of the depots increase, the mechanical strength of the strut may decrease. Additionally, a longer sustained release of drug delivery media may be facilitated by a larger depth $D_1$. A diameter $D_2$ of cylindrical depot 128 may have a range from about 10% to about 95%, about 20% to about 80%, 30% to about 70%, or about 40% to about 60% of width $W_1$.

Additionally, the geometrical parameters that characterize depots such as size (e.g., depth, diameter, etc.) and shape may be configured to facilitate treatment of an inflammatory response. For example, the geometry of depots may be configured to maximize sustained delivery of anti-inflammatory agent throughout the degradation of a device to counteract the inflammatory effect of degradation by-products.

A single depot or plurality of depots may be formed as a laser trench or laser trenches on a body of an implantable medical device such as stent 1 by exposing a surface of the device to an energy discharge from a laser, such as an excimer laser. Alternative methods of forming depots include, but are not limited to physical or chemical etching techniques. Techniques of laser fabrication or etching to form depots are well-known to one of ordinary skill in the art. Depots can be formed in virtually any stent structure and not merely the above-described structure.

Figure 4A:
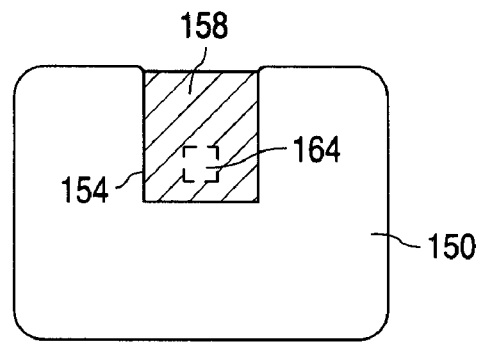
FIGS. 4A-B illustrate cross-sections of struts with a depot filled with a delivery media.
Figure 4B:
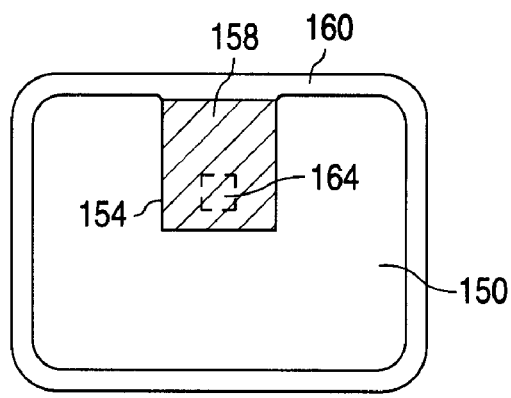

FIG. 4A illustrates a cross-section of a strut 150 with a depot 154 filled with delivery media 158. FIG. 4B illustrates another embodiment in which depot 158 can be covered by a coating 160. Coating 160 can be a degradable polymer coating that can delay the release of delivery media 158 from depot 154. Alternatively, a protective sleeve can be disposed over or within a stent to reduce or prevent premature delivery of the delivery media. The sleeve can be removed prior to or after implantation to allow erosion of the stent and delivery of the delivery media. The sleeve can be sized to have a slip or friction fit over a crimped stent. Such a sleeve could be made from biostable, biodegradable, or biosoluble polymers. In exemplary embodiments, the sleeve can be made of biostable elastomeric polymers such as poly ether block amides, for example, Pebax® from Arkema, Inc. of Philadelphia, Pa. In other exemplary embodiments, the sleeve can be formed from biodegradable elastomeric polymers such as polycaprolactone or poly(tetramethylene carbonate).

In some embodiments, coating 160 or a protective sleeve can include a dispersed active agent. The active agent(s) is the coating can be the same or different from the active agent in the delivery media. For example, in one embodiment, the delivery media can have an anti-inflammatory agent and the coating can have an anti-proliferative, or the reverse.

Figure 5A:
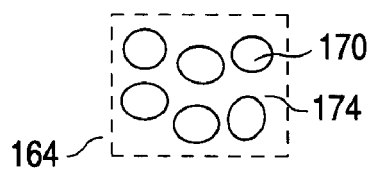
FIGS. 5A-B is a schematic illustration of an expanded section of a delivery media showing particles of delivery media.
Figure 5B:
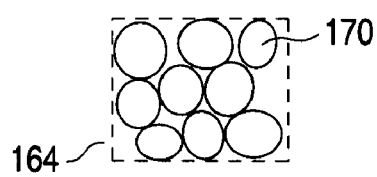

In certain embodiments, the delivery media can be incorporated into a depot with a binder that holds the individual particles of delivery media together and within the depot. FIG. 5A is a schematic illustration of an expanded section 164 of delivery media 158 showing particles 170 of delivery media that are dispersed within an erodible binder 174. The amount of delivery media can be varied through ratio of particles to binder material. For example, FIG. 5B depicts an embodiment showing particles 170 with little or no binder material. Such an embodiment may allow the largest amount of delivery media delivered to a patient. The binder material may be a coating on the surface of the particles that allows the particles to adhere to each other and the depot walls so that the particles remain in the depot at least until implantation of the stent. For example, the coating can include a hydrogel or a water soluble polymer. A coating over the opening of the depot can be used to contain particles having no binder material in the depot.

Since the particles are released as the binder material erodes or dissolves, the rate of the release of particles can be varied or controlled through selection of binder material. A fast eroding polymer or water soluble polymer can be selected to result in a fast or burst release of particles. A slower eroding polymer can be selected to obtain a slow or gradual release of particles. As mentioned above, the release of delivery media can be delayed by a coating layer over the opening of the depot, as depicted by coating 160 in FIG. 4B.

In alternative embodiments, the delivery media can be in the form of a suspension within a depot. For instance, delivery particles can be suspended within a fluid, such as an aqueous solution or other biocompatible fluid. In such an embodiment, the opening of the depot can be covered by an erodible coating, such as depicted by coating 160, to reduce or prevent flow of the suspension from the depot. The amount of delivery media can be varied through the ratio of particles to solution. The release profile in such embodiments can be configured to be a pulse release since the particles of delivery media may tend to rapidly flow out of the opening once a coating over the opening degrades away. "Pulse release" generally refers to a release profile that features a sudden surge of the release rate of the delivery media. The release rate surge of the delivery media would then disappear within a period. A more detailed definition of the term can be found in Encyclopedia of Controlled Drug Delivery, Edith Mathiowitz, Ed., Culinary and Hospitality Industry Publications Services.

In some embodiments, depots may be selectively distributed at or near portions of a surface of a stent depending upon the type of treatment desired. In such embodiments, a stent may have depots selectively distributed along a longitudinal axis. For example, a stent can have more depots or only have depots at a distal end, proximal end, or center portion.

Depots may also be selectively or directionally disposed on abluminal faces, luminal faces, both abluminal and luminal faces, and sidewalls of a stent. Selectively disposing particles in this manner may allow for directional release of the particles and drug release to targeted region. As discussed with reference to FIG. 2A, delivery particles can be released from an abluminal depot into the vascular wall tissue after implantation. Delivery particles are released from luminal depots into the blood stream for treatment of distal vasculature after implantation.

In some embodiments, an active agent for a delivery particle may be released by osmotic pressure. In this embodiment, the active agent or delivery media is disposed in a well cut into a strut of a stent. FIG. 6A depicts an overhead view of a stent strut 200 with a well 204 containing active agent or delivery media. The well may be covered with a coating layer with an opening over well 204. FIG. 6B depicts a side view of strut 200 showing a coating layer 208 disposed above well 204. Coating layer 208 has an opening 210 to allow delivery of active agent or delivery particles from well 204. The difference in concentration of active agent or delivery particles, or an additive such as a salt, in well 204 and outside of well 204 creates an osmotic pressure gradient. This gradient provides for a controlled delivery of active agent or delivery particles through the opening. The opening can be directed either luminally or abluminally.

In further embodiments, an implantable medical device adapted for both local and regional treatment includes a substrate formed from a corrodible metal with a coating including the releasable delivery media that allows for sustained release of active agent(s). The coating can be above at least a portion of the substrate.

In some embodiments, the coating can include a delivery media, such as particles, dispersed in an erodible binder material. Upon implantation, the erosion or dissolution of the binder causes a release of delivery media, such as particles, into the body. The amount of delivery media can be varied through the ratio of delivery media to binder material. FIG. 7A depicts a delivery media layer 234 over a corrodible metallic substrate 230. FIG. 7B depicts an expanded portion 236 of layer 234 which shows delivery particles 238 dispersed in an erodible binder material 8. As binder material 8 erodes, particles 238 are released into the body and can be transported to distal vasculature for treatment. As depicted in FIG. 7C, an erodible topcoat layer 242 can be disposed above the delivery media coating layer 234 to delay the delivery of the delivery layer. The release of the delivery particles can be controlled by erosion rate of the binder material, the faster the erosion, the faster the release of particles.

In certain embodiments, the coating can be selectively disposed on abluminally or luminally to allow for directional release of delivery media. Referring to FIG. 2, delivery particles can be released from an abluminal layer into the vascular wall tissue after implantation. A luminal coating allows release of drug delivery particles into the blood stream for treatment of distal vasculature after implantation.

In additional embodiments, an implantable medical device adapted for both local and regional treatment includes a substrate formed from an erodible polymer which includes releasable delivery media that allows for sustained release of active agent dispersed within the substrate. As described herein, the delivery media can include particles that are adapted for sustained release of an active agent. A device substrate having dispersed delivery media can be particularly advantageous since it allows release of the delivery media such as particles during all or most of the degradation time of the substrate.

A device substrate with dispersed delivery media can be formed from a polymer construct that is fabricated with dispersed particles. Delivery particles can be blended with a polymer melt and then the melt can be extruded to form a construct, such as a tube A device can then be formed from the construct, for example, a stent pattern can then be cut into a tube by laser machining the tubing.

In some embodiments, a substrate loaded with delivery particles can also include depots filled with delivery particles or a coating that includes delivery particles. In an embodiment, the substrate can have particles with a different type of agent or drug, or mixture thereof, than a coating or depot. A coating having a different agent or drug, or mixture thereof, can allow staged release of different agents or drugs during different time periods. A depot having a different agent or drug can allow release of different agents or drugs during overlapping time frames.

Any biocompatible polymer suitable for a given treatment may be selected for use in a device, such as a stent. The release profile of delivery media from the substrate can be controlled by the concentration of delivery particles in the substrate and the erosion rate of the erodible polymer. In certain embodiments, the erosion rate of the polymer can be tailored through employment of suitable copolymers and polymer blends. Representative polymers include, but are not limited to, poly (L-lactide), poly(glycolide), poly(DL-lactide), poly($\epsilon$-caprolactone), poly(trimethylene carbonate), poly(dioxanone), and copolymers and blends thereof. Exemplary copolymers include, but are not limited to, 90:10 poly(L-Lactide-co-glycolide); 50:50 poly(L-Lactide-co-glycolide); 70:30 poly(L-lactide-co-$\epsilon$-caprolactone); 70:30 poly(L-lactide-co-DL-lactide); 70:30 poly(L-lactide-co-trimethylene carbonate); and 70:30 poly(L-lactide-co-dioxanone).

In further embodiments, a substrate of a device can have two or more different polymer layers, with at least one layer including dispersed delivery media. In one embodiment, the type of polymers can be the same or different with the layers differing by the type of delivery media. A stent formed with a layered structure can be advantageous, since a layered structure tends to enhance the mechanical stability of a construct.

FIG. 8 depicts a cross-section of strut 250 of a stent with polymer layers 252, 254, and 256. As an example, layers 252 and 256 can have the same type of delivery media while layer 254 has a different delivery media or no delivery media. The polymer of layer 254 may be selected to be stiff and strong to provide mechanical support, while layers 252 and 256 may be selected for to provide flexibility or to provide a selected erosion rate for delivery of the delivery media. Polymer layers can be formed by coextrusion of a tube, followed by cutting of a pattern in the layered tube.

In additional embodiments, the erosion rate of a stent substrate can be modified by including filler materials in the polymer so that it has basic degradation products. When a hydrolytically degradable polymer degrades through hydrolysis, the resulting acidic end groups in the polymer have a tendency to increase the degradation rate through an autocatalytic effect. The influence of basic filler materials on the degradation of amorphous D- and L-lactide copolymer has been previously demonstrated. S. A. T. van der Meer et al., Journal of Materials Science: Materials in Medicine, Volume 7, No. 6, June, 1996. In particular, it was shown that the use of hydroxyapatite as a filler material decreases the degradation rate of the filled polymer. The ability to tune the degradation rate of a polymer system to the clinical need of the system dramatically extends the range of polymers that can be employed in a particular application.

In additional embodiments, a device such as a stent adapted for both local and regional treatment may include a scaffolding with two or more layers, such that at least one layer is a corrodible metal and at least one layer is an erodible polymer. As stated above, a stent formed with a layered structure can be advantageous, since a layered structure tends to enhance the mechanical stability of a construct. A variety of combinations of metal and polymer layers in terms of the number of layers, arrangement of layers, types of material can be envisioned depending on course of treatment desired. A layered scaffolding can have three or more layers with alternating metallic and polymeric layers. The outermost, abluminal and luminal layers, can both be metal, one metal and one polymer, or both polymer.

A scaffolding with metal and polymer layers with drug delivery media can be formed from a tubing with metal and polymer layers. Such tubing can be formed through coextrusion of polymer layers around or within a metal tube, wicking between metallic tubing pieces that are coaxially oriented (one inside other with a clearance in between). Delivery particles can be blended with the polymer melt that is used to form the layers. Additionally, metallic tubes can be dip coated or sprayed to form a coating over the metallic tube. The coating material includes a polymer dissolved in a solvent. Delivery particles can also be included within the coating material. The polymer-coated metallic tube is formed by removing the solvent. The coated metallic tubes can then be slid into each other with the metal surface coated with a solvent or other adhesive agent on the side contacting the polymer. The adhesive can be an adhesive that is activated through heat or vibration. The polymer and metal layers can be uniform in thickness or vary in thickness along the length of the tube. The stent pattern can then be cut by laser machining the tubing.

Embodiments of layered scaffolding can allow for staged release of the delivery media due to differences in degradation rate of the layers. Staged release refers to release of the delivery media over two or more discrete time intervals which may or may not be overlapping. The type of agent and/or drug released in the different time periods can be the same or different.

In some embodiments, a metal or polymer layer can include releasable delivery media, as described above. In one such embodiment, a layer can have depots filled with releasable delivery media. In another such embodiment, the layered structural element can have a coating including releasable delivery media. FIG. 9 depicts a cross-section of a layered strut 260 having a metal abluminal or luminal layer 261 and a polymer abluminal or luminal layer 262. The layers can also include depots 266 and 264 that can be filled with releasable delivery media. A coating layer 268 is disposed above the layers and can act as a top-coat layer or can also include releasable delivery media. In an embodiment, a metal and polymer can be selected so that the polymer erodes faster than the metal layer. Therefore, the metal can provide structural support to the scaffolding during a substantial portion of the time of release of the delivery media.

Figure 10:
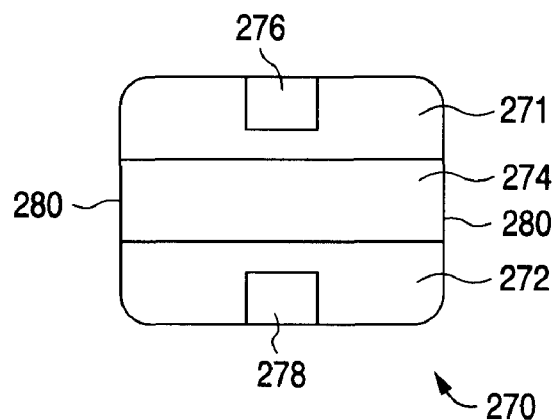
FIG. 10 depicts a cross-section of a three layer strut.

FIG. 10 depicts a three layer strut 270 with metal outer layers 271 and 272 and an inner polymer layer 274. Metal layers 271 and 272 have depots 276 and 278, respectively, filled with releasable delivery media. Polymer layer 274 can have releasable delivery media dispersed within the layer. The release of a the delivery media from the metal layers and the polymer layers may occur in a staged fashion since a majority of the polymer layer 274 is covered by metal layers 271 and 272. Two or more stages of release of the delivery media can be provided by additional inner layers.

It may be desirable to delay the erosion of one or more layers during release of the delivery particles. Delaying the erosion of a layer maintains the mechanical properties of the stent for a longer period of time. Certain embodiments that allow delayed erosion of a layer can include a structural element having an erodible polymer layer between two metallic layers that are not formed of self-dissolving metals. The two metallic layers can be a galvanic couple, such that the metallic layers can undergo galvanic dissolution in bodily fluids when the layers come into contact.

Figure 11A:
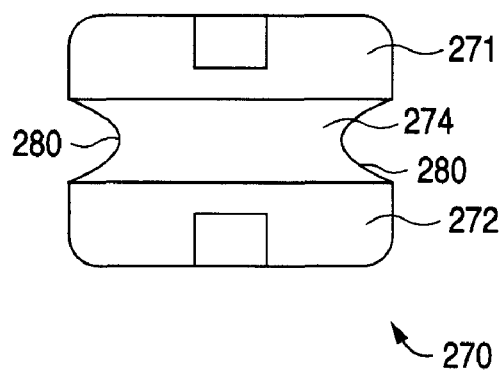
FIG. 11A depicts a cross-section of a three layer strut with a center layer partially eroded.
Figure 11B:
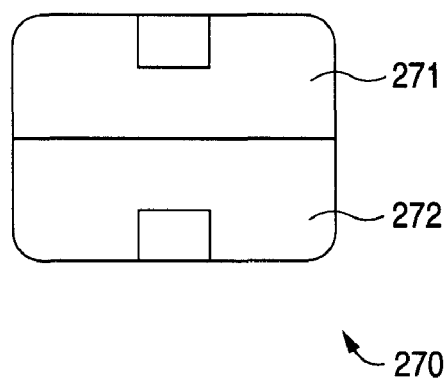
FIG. 11B depicts a cross-section of a layered strut after collapse of a middle layer.

FIG. 10 can be used to illustrate these embodiments. Metallic layers 271 and 272 can be a galvanic couple, which undergo galvanic dissolution in a bodily fluid when in contact. Polymer layer 274 erodes preferentially at sidewalls 280 due to exposure to bodily fluids, as illustrated in FIG. 11A. Additionally, the interior of polymer layer 274 can also erode and the mechanical properties degrade due to diffusion of fluid within polymer layer 274. The degree of diffusion depends on the polymer. Polymers having a high diffusion rate of moisture can be characterized as bulk eroding. Such polymers can exhibit little loss of mass even with a substantial decrease in mechanical properties. The loss of mass and mechanical properties of polymer layer 274 can cause a collapse of polymer layer 274, resulting in contact in between metal layers 271 and 272, as depicted by FIG. 11B. Upon contact, metal layers 271 and 272 undergo galvanic corrosion.

As discussed above, a polymer scaffolding of a stent with dispersed delivery media can be fabricated from tubing formed by melt extrusion with dispersed delivery particles. Additionally, polymer layers of a scaffolding of a stent with dispersed delivery media can be formed from tubing made through coextrusion of the polymer layers.

However, active agents included with drug delivery media may be susceptible to degradation at elevated temperatures. For example, some active agents tend to degrade at temperatures above about 80° C. to 100° C. Thus, it would be desirable to process the polymer and delivery particles at lower temperatures to reduce or prevent degradation of the active agents.

Some embodiments of the present invention can include gel processing of polymers with dispersed delivery media in forming implantable medical devices, such as stents. An important advantage of gel processing is that it allows processing of polymers at temperatures substantially below the melting temperatures of polymers. A "polymer gel" generally refers to a polymer network swollen or capable of being swollen in a liquid. The polymer network can be a network formed by covalent bonds or by physical aggregation with regions of local order acting as network junctions. For example, a physical crosslinked network can be a network of microcrystalline domains in a polymer that act as physical crosslinks or net points.

In some embodiments, the gel can be processed at or near ambient or room temperature. Embodiments can include employing gel processing in fabricating constructs, such as tubes, for stent scaffoldings. Gel processing can also be used to process coatings. In gel processing, a mixture of polymer and solvent that forms a gel is processed.

A representative example of a physically aggregated polymer gel is poly vinyl alcohol (PVA) and swollen with water. In one embodiment, a PVA-water gel is produced from PVA with a high degree of hydrolysis and water. The degree of hydrolysis can be greater than 70%, 80%, or greater than 90%. A gel can be formed by dissolving the PVA in water at a temperature of about 90° C. and then cooling the solution. Gel formation is a function to time, which can be accelerated using a freeze—thaw process. The PVA-water gel includes microcrystalline domains that act as physical cross-links.

Another example of a physically aggregated gel is a block copolymer of poly(L-lactide-glycolic acid) (PLGA) swollen with benzyl benzoate, ethyl benzoate, or benzyl alcohol. Such gels typically are about 50% PLGA and 50% solvent (biocompatible). Such gels can be further include active agents in the range of 10-30%. In some embodiments, a polymer and solvent combination are selected that are capable of forming a gel. The polymer and solvent can be mixed to form a gel in a mixing apparatus, such as a batch mixer or extruder. Active agents, including drug delivery media described above, can be mixed with the gel. The gel mixture can be processed in a forming apparatus such as an extruder to form a polymer construct such as a tube.

The temperature of the gel in the mixing or forming apparatus can be low enough that there is little or no degradation of active agents within the gel. In one embodiment, the temperature is less than a melting temperature of the polymer in the gel, for example, at or about room temperature.

In accordance with this invention, a portion of a stent scaffolding or stent coating may be formed from a mixture of multiple solutions. A mixture of multiple solutions provides for one or more dispersed phases within the stent scaffolding or stent coating. These phases may include a delivery media, such as polymeric particles, and a binder material, such as a polymeric matrix.

Producing a mixture of multiple solutions includes several steps. A first polymer is dissolved within a first solvent to produce a first phase. A second polymer is dissolved in a second solvent to produce a second phase. The individual phases are then combined to form a mixture. Immiscible solvents may be chosen to control the proportions at which the solution mix. Due to the immiscibility of the solvents, the mixture may be heterogeneous, however it is contemplated that in some embodiments the mixture could be homogeneous. This would depend upon the proportion of solutions used.

The mixture may be applied directly to a stent surface (i.e. scaffold, strut, depot or cavity formed in a strut, etc.) as a coating or it may be processed further in order to form a tube that a stent may be fabricated from. Direct coating of a stent surface can be accomplished through processes that are well known in the art, such as spray coating, dip coating, or brush coating. It is further contemplated that processes such as electrophoresis may be suitable for depositing the coating mixture onto the surface of a stent. Likewise, processes for producing tubing from a solution are well known and may be employed to form a tube for stent fabrication. Extrusion is one such process, as is molding. In either instance, after drying or removal of some or all of the solvents, a more solid mixture of the delivery media and the binder material will be created.

The mixture can also be adapted to include active agents such as anti-inflammatories, antiproliferatives, and other bioactive agents. These agents may be disposed within either phase of the mixture. For example, the agents may be incorporated into polymeric particles through encapsulation, or it may be incorporated within a polymeric matrix. Upon erosion of the mixture after stent implantation, the delivery media or binder material may erode and release into the patient body. Through this erosion, active agents may also be delivered into the patient body to provide therapeutic effect.

There are a number of different polymers and solvents that may be chosen to form a mixture of multiple solutions in the manner described above. By way of example, the first phase of the mixture may be formed by dissolving poly-lactic acid (PLA) in cyclohexane and the second phase of the mixture may be formed by dissolving poly-ester-amide (PEA) in methanol. It is contemplated that the solvents may be organic or inorganic compounds. Also, the resulting solutions may or may not be aqueous.

The immiscibility of the solvents used in this process is a determinant of the proportion of the polymers in the mixture of multiple solutions. Thus, forming a mixture of polymers in this way provides an advantage in manufacturing. That is, maintaining control over the dispersion of delivery media within a binder material can be accomplished more easily since it can be done indirectly through the choice of polymers and solvents rather than by directly dispersing one polymer within another while processing the polymers simultaneously.

In an alternative embodiment, a mixture such as the one described above may be used to form a coating on a non-stent medical device such as a balloon or guidewire. The properties of such a coating would allow for the adaptation of those medical devices for improved functional and performance characteristics such as drug delivery, lubricity, or wetting characteristics.

Representative examples of forming apparatuses can include, but are not limited to, single screw extruders, intermeshing co-rotating and counter-rotating twin-screw extruders, and other multiple screw masticating extruders. As the gel is conveyed through the forming apparatus, at least some of the solvent may be vaporized and removed. The gel can then be conveyed through a die to form a polymeric construct, such as a tube.

In certain embodiments, after formation of a construct from the gel, the construct can be dried by removal of some or all of the solvent from the gel. After drying, the construct exhibits the physical properties of the polymer or polymer formulation, but without the solvent that was selected for gelation. In some embodiments, at least some of the solvent in the construct is allowed to remain in the construct. The solvent can elute or diffuse out of the device formed from the construct in vivo upon implantation. In some embodiments, the device is formed from a polymer that does not swell when exposed to bodily fluids. Alternatively, a device can be formed from a polymer that swells upon exposure to bodily fluids.

The formed polymeric part can be dried or cooled by contacting the formed polymeric construct with a cooling fluid having a selected temperature. For example, the formed polymeric construct can be cooled in a quench bath to remove solvent from the gel. Alternatively, the formed polymeric construct may be cooled by air or some other gas at a selected temperature. Some examples of cooling fluids include, but are not limited to, isopropyl alcohol, chloroform, acetone, water, and any mixtures thereof in any proportion.

Representative examples of polymers that may be used for a substrate, binder, coatings, and drug delivery media to fabricate embodiments of implantable medical devices disclosed herein include, but are not limited to, poly(N-acetylglucosamine) (Chitin), Chitosan, poly(3-hydroxyvalerate), poly (lactide-co-glycolide), poly(3-hydroxybutyrate), poly(4-hydroxybutyrate), poly(3-hydroxybutyrate-co-3-hydroxyvalerate), polyorthoester, polyanhydride, poly (glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly (glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly (vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

Representative examples of biosoluble materials that may be used for a substrate, binder, coatings, and drug delivery media to fabricate embodiments of implantable medical devices disclosed herein include, but are not limited to, poly (ethylene oxide); poly (acrylamide); poly (vinyl alcohol); cellulose acetate; blends of biosoluble polymer with bioabsorbable and/or biostable polymers; N-(2-hydroxypropyl) methacrylamide; and ceramic matrix composites.

Delivery media may incorporate active agent(s) such as anti-inflammatories, antiproliferatives, and other bioactive agents.

An antiproliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbot Laboratories, Abbot Park, Ill.), prodrugs thereof, co-drugs thereof, and combinations thereof. In one embodiment, the anti-proliferative agent is everolimus.

An anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnarnate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. In one embodiment, the anti-inflammatory agent is clobetasol.

Alternatively, the anti-inflammatory may be a biological inhibitor of proinflammatory signaling molecules. Anti-inflammatory biological agents include antibodies to such biological inflammatory signaling molecules.

In addition, the particles and binder may include agents other than antiproliferative agent or anti-inflammatory agents. These active agents can be any agent which is a therapeutic, prophylactic, or a diagnostic agent. In some embodiments, such agents may be used in combination with antiproliferative or anti-inflammatory agents. These agents can also have anti-proliferative and/or anti-inflammmatory properties or can have other properties such as antineoplastic, antiplatelet, anti-coagulant, anti-fibrin, antithrombonic, antimitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting.

Other bioactive agents may include antiinfectives such as antiviral agents; analgesics and analgesic combinations; anorexics; antihelmintics; antiarthritics; antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other active agents which are currently available or that may be developed in the future are equally applicable.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of forming a coating material comprising:
   forming a first non-aqueous solution from a first polymer dissolved in a first solvent;
   forming a second non-aqueous solution from a second polymer dissolved in a second solvent, wherein the second solvent is immiscible with the first solvent; and
   forming a mixture from the first non-aqueous solution and the second non-aqueous solution;
   wherein the mixture comprises polylactic acid (PLA), poly-ester-amide (PEA), cyclohexane, and methanol.

2. The method of claim 1 further comprising adding an active agent into the mixture.

3. A method of forming a coating on a medical device comprising:
   forming a first non-aqueous solution from a first polymer dissolved in a first solvent;
   forming a second non-aqueous solution from a second polymer dissolved in a second solvent, wherein the second solvent is immiscible with the first solvent;
   forming a mixture from the first non-aqueous solution and the second non-aqueous solution;
   applying the mixture to a surface of a medical device; and
   removing the first and second solvents from the mixture to form a medical device coating;
   wherein the mixture comprises PLA, cyclohexane, PEA, and methanol.

4. The method of claim 3 wherein applying the mixture to the surface of the medical device comprises spraying the mixture onto the surface of the medical device.

5. The method of claim 3 wherein applying the mixture to the surface of the medical device comprises immersing the surface of the medical device in the mixture.

6. The method of claim 3 wherein the medical device coating comprises a particles comprising the first polymer dispersed in a matrix comprising the second polymer.

7. The method of claim 3 wherein the surface of the medical device is disposed within a cavity formed in the medical device.

8. The method of claim 3 wherein the medical device is a stent, a balloon, or a guidewire.

9. The method of claim 8 wherein the medical device is adapted to erode when implanted within a patient's body.

10. A method of forming a coating on a medical device comprising:
    forming a first non-aqueous solution from PLA dissolved in cyclohexane;
    forming a second non-aqueous solution from PEA dissolved in methanol;
    forming a mixture from the first non-aqueous solution and the second non-aqueous solution;
    applying the mixture to a surface of a medical device; and
    removing the cyclohexane and methanol from the mixture to form a medical device coating.

11. The method of claim 10 wherein the medical device coating comprises particles comprising PLA dispersed in a matrix comprising PEA.

12. The method of claim 10 wherein the medical device coating comprises particles comprising PEA dispersed in a matrix comprising PLA.

* * * * *